US012717407B2

(12) United States Patent
Combier et al.

(10) Patent No.: US 12,717,407 B2
(45) Date of Patent: Aug. 25, 2026

(54) EYEWEAR FOR DETERMINING AN EYE DIRECTION

(71) Applicant: Essilor International, Charenton le Pont (FR)

(72) Inventors: Jessica Combier, Charenton le Pont (FR); Aude Bouchier, Charenton le Pont (FR); Jean-Paul Cano, Charenton le Pont (FR)

(73) Assignee: Essilor International, Charenton le Pont (FR)

( * ) Notice: Subject to any disclaimer, the term of this patent is extended or adjusted under 35 U.S.C. 154(b) by 0 days.

(21) Appl. No.: 19/278,418

(22) Filed: Jul. 23, 2025

(65) Prior Publication Data

US 2025/0348143 A1 Nov. 13, 2025

Related U.S. Application Data

(62) Division of application No. 18/551,058, filed as application No. PCT/EP2022/058624 on Mar. 31, 2022, now Pat. No. 12,399,557.

(30) Foreign Application Priority Data

Mar. 31, 2021 (EP) .................................... 21305406

(51) Int. Cl.
*G09G 5/00* (2006.01)
*A61B 3/113* (2006.01)
*G06F 3/01* (2006.01)

(52) U.S. Cl.
CPC .............. *G06F 3/013* (2013.01); *A61B 3/113* (2013.01)

(58) Field of Classification Search
CPC ......... G09G 3/3258; G09G 2300/0426; G09G 2300/0842; G09G 2310/061; G09G 2310/08; G02B 27/0093; G02B 27/0081; G02B 27/0172
USPC .......................................................... 345/156
See application file for complete search history.

(56) References Cited

U.S. PATENT DOCUMENTS

2016/0044253 A1* 2/2016 Dainty .................. G02B 5/208 348/335
2020/0355929 A1* 11/2020 Zhang .................. G02B 27/425
2021/0068652 A1* 3/2021 Nistico .................. A61B 3/113
2021/0173547 A1* 6/2021 Mak .................... G06F 3/04845
2024/0012477 A1* 1/2024 Thieberger ............. G06F 3/013

OTHER PUBLICATIONS

International Search Report & Written Opinion mailed on Jul. 8, 2022 in PCT/EP2022/058624 filed on Mar. 31, 2021 (14 pages).

* cited by examiner

*Primary Examiner* — Jennifer T Nguyen
(74) *Attorney, Agent, or Firm* — Oblon, McClelland, Maier & Neustadt, L.L.P.

(57) ABSTRACT

An eyewear is adapted for fitting a user's face and for determining an eye direction of a user's eye. The eyewear is provided with at least three light sensors each configured for outputting a measured light intensity value that corresponds to ambient light originating from surroundings of the user outside the eyewear and reflected or scattered by the user's eye. Processing circuitry of the eyewear determines the eye direction from the measured light intensity values.

6 Claims, 5 Drawing Sheets

EYEWEAR FOR DETERMINING AN EYE DIRECTION

CROSS REFERENCE TO RELATED APPLICATIONS

This application is a divisional Application of U.S. application Ser. No. 18/551,058, filed Sep. 18, 2023, which is a National Stage application of PCT/EP2022/058624, filed Mar. 31, 2022, and claims priority to European Priority application Ser. No. 21/305,406.7 filed Mar. 31, 2021. The entire contents of the above-identified applications are incorporated herein by reference.

The invention relates to an eyewear adapted for determining an eye direction.

BACKGROUND OF THE INVENTION

Determining the direction of at least one eyeball of a person is useful for many applications, for example in the ophthalmic field, the augmented reality field, etc. Generally for these applications, energy consumption and reliability of the determined eyeball direction are important issues, and the solutions proposed up to now are still not satisfactory.

Indeed, some of the existing solutions implement array-type image sensors that are arranged for capturing images of the pupil, and processing units configured for inferring the eyeball direction from the captured images. But such image sensors are energy-consuming, so that they require power sources with enough capacity to be provided. Such power sources are heavy and cumbersome, and combining them with an ophthalmic eyewear or an augmented reality equipment is difficult, resulting in devices which are unpleasant when worn for long periods.

In addition, many of the existing solutions implement light sources arranged in the vicinity of the eyeball for emitting infrared light towards the user's eye. Such light sources improve the reliability of the eyeball direction that is determined, in particular when the ambient light level is low. But these light sources further increase the energy consumption, making the issue of the weight and size of the power source even more critical.

Starting from this situation, one object of the present invention consists in providing a new device that allows determining the eyeball direction, but without the drawbacks of the existing ones.

In particular, the present invention aims at providing a device capable of determining the eyeball direction, that is simple, lightweight and easy to arrange within a face-fitting equipment.

Another object of the present invention is to provide such device that determines the eyeball direction in a reliable manner, for most of ambient light conditions.

SUMMARY OF THE INVENTION

For meeting at least one of these objects or others, an aspect of the present invention proposes an eyewear adapted for fitting a user's face and for determining an eye direction of a user's eye, this eyewear comprising:

at least three light sensors arranged in the eyewear for this user's eye, each of the light sensors being configured for outputting for each determination of the eye direction, at least one measured light intensity value that corresponds to ambient light originating from surroundings of the user outside the eyewear and reflected or scattered by the user's face within a field of view effective for this light sensor; and a processing unit arranged for receiving the measured light intensity values for each determination of the eye direction, and for determining the eye direction from these measured light intensity values.

According to the invention, the light sensors are arranged so that, when the eyewear is worn by the user:

each field of view relating to one of the light sensors has an apex at the eyewear and a cross-section increase direction oriented towards the user's face, this field-of-view cross-section increasing continuously from the eyewear towards the user's face, each field of view contains at least part of the user's eye, and each field of view has an integrated aperture value that is comprised between 0.006 steradian and 0.22 steradian, and the user's eye occupies at least 30%, preferably at least 50%, of this field of view.

Thanks to measuring ambient light that is reflected or scattered by the user's face, and because the field of view of each light sensor is comprised between 0.006 steradian and 0.22 steradian, the invention eyewear combines low energy consumption and reliability in determining the eyeball direction. In this way, it is unnecessary using light sources embedded within the eyewear.

In addition, using light sensors that are each comprised of one photodetector, instead of array-type sensors, also reduces the energy consumption.

The solid-angle range from 0.006 steradian to 0.22 steradian for each sensor field-of-view constitutes a trade-off between this field of view being large enough for collecting enough light, and being limited for corresponding to a portion of the user's face that contains significant information about the eyeball direction. Fields of view larger than 0.22 steradian would cause the information about the eye direction to be diluted, thereby reducing the reliability of the eye direction determination. Because each field-of-view cross-section increases continuously from the eyewear towards the user's face, the light sensors do not operate through imaging of parts of the user's face on each of these sensors.

In various embodiments of the invention, each light sensor may comprise a photodiode, a phototransistor, an ambient light sensor, a photovoltaic cell, etc. In a known manner, an ambient light detector is comprised of a light sensor combined with a photopic filter. Similarly, any detector used for each light sensor may be combined with a notch filter centered on a desired wavelength value, or also with a polarization filter, etc.

Generally for the invention, a number of the light sensors may be comprised between four and eight, including four and eight light sensors. Such range for the sensor number is an optimized trade-off between some limited redundancy for reliability of each determination of the eye direction and reduction of the energy consumption.

Preferably, each light sensor of the invention eyewear may be sensitive to visible light. Indeed, sensor sensitivity limited to visible light increases detection contrast, so that determination reliability for the eye direction is further improved.

In possible implementations of the invention, the respective fields of view of the at least three light sensors may have conical shapes with circular cross-sections. For such configuration, aperture angles ($2\cdot\theta$) of each of these fields of view may be advantageously comprised between 5° and 30°, preferably between 8° and 15°.

The invention eyewear may comprise a see-through area which is dedicated to the user's eye when the eyewear is worn by the user. Then, each light sensor may be located near a peripheral edge of the see-through area, or light from the user's face may be reflected towards the light sensors by a holographic mirror that extends across the see-through area.

In various embodiments of the invention, the eyewear may comprise at least one of the following components for determining the field of view of each light sensor:

- a lens, either of refractive type or of diffractive type, with fixed focal length and coupled to the light sensor;
- a variable focal lens, for example a variable membrane lens or a liquid crystal lens or a variable refractive index lens, that is coupled to the light sensor, this variable focal lens having a focal length value which is adjusted by a controller of the eyewear;
- an optical fiber segment that is coupled to the light sensor; and
- a hole with slanted peripheral wall or an aperture stop that is arranged above a photosensitive surface of the light sensor.

For improved reliability of the determination of the eye direction, it is advantageous that the measured light intensity values which are outputted by the light sensors oriented towards the user's eye exhibit limited or low redundancy. For this purpose, the fields of view of these light sensors are preferably different. To this end, respective axial directions of a first subset of these fields of view may all pass through one first common convergence point located within the user's eye, and another subset of these fields of view may all pass through one second common convergence point also located within the user's eye, these first and second common convergence points being located at different depth values within the user's eye when the eyewear is worn by the user. But generally, it may be preferred that the light sensors are arranged so that a ratio of a sum of aperture values of field-of-view portions that are each common to at least two of the fields of view, is less than 40%, preferably less than 10%, of a sum of the respective aperture values of all the fields of view.

Optional improvements of the invention eyewear are listed hereafter, which may be implemented separately or in combination of several of them:

- the processing unit may be configured for calculating a normalized deviation value from each measured light intensity value, this normalized deviation value equaling a result of a difference between the measured light intensity value and a mean value of the measured light intensity values used for one and same determination of the eye direction, divided by this mean value. Then, the processing unit may be further configured for determining the eye direction from the normalized deviation values;
- the light sensors may be arranged so as to determine pairs of fields of view, with each pair containing two fields of view having common axial direction and apex but different aperture values. Then, the processing unit may be configured to calculate for each pair a combination, for example a difference or a ratio, between the respective light intensity values measured for both fields of view of this pair, and to determine the eye direction from results of the differences related to at least three pairs of fields of view. Alternatively, the respective light intensity values measured for both fields of view of each pair may be used directly by the processing unit for determining the eye direction. For example, when the fields of view are conical with circular cross-sections, respective aperture angles of both fields of view of each pair may be of about 40° and 10°;
- the eyewear may further comprise additional light sensors with respective fields of view that are oriented away from the user's eye when the eyewear is worn by the user, and that are dedicated to assessing a light map of the user's surroundings and/or of the user's face. Such additional light sensors may be oriented away from the user's face and/or towards a portion of the user's face skin. Then, the processing unit may be configured to determine the eye direction from the measured light intensity values relating to the light reflected or scattered by the user's eye in combination with the light map as assessed by the additional light sensors; and
- the processing unit may be configured to determine the eye direction using one of the following algorithm types:
  - regression type, in particular linear and polynomial regression, support vector regression, neural network type;
  - nearest neighbor method, gaussian process and correlation method;
  - an algorithm based on a 3D-model of the user's face and/or of the light sensor arrangement in the eyewear; and
  - combinations of at least two of the preceding types.

Possibly, the invention eyewear may be configured to output successive sets of measured light intensity values, each set corresponding to a respective eye direction determination sequence. Then, the processing unit may be configured to determine successive filtered eye directions by implementing a time-filter, in particular a Kalman filter, either with the successive sets of measured light intensity values, or with successive eye directions as determined each separately from one of the successive sets of measured light intensity values. Further improved reliability is thus obtained for each eye direction that is determined.

The eyewear may also be configured to perform a calibration step prior to useful operation for determining the eye direction, the calibration step consisting in acquiring labeled training sets which are each comprised of measured light intensity values and a corresponding eye direction, and adjusting parameters of an algorithm that is implemented by the processing unit for the useful operation of determining the eye direction, based on the labeled training sets. Such calibration step may constitute a general training or an individualized training that is dedicated to the user who wears the eyewear.

Generally, the invention eyewear may be of one among the following types:

- spectacles provided with electrochromic lenses, and adapted for adjusting a transmission of each lens based on the eye direction determined for the corresponding user's eye, and optionally also based on a sensed direction of a light source in the user's surroundings;
- a mask provided with an electrochromic glass, and adapted for adjusting an absorption of the glass based on the eye direction determined for at least one of the user's eyes, and optionally also based on a sensed direction of a light source in the user's surroundings;
- an augmented reality eyewear, an informative eyewear or a mixed reality and virtual reality eyewear;
- an eyewear, for example spectacles, mask or goggles, provided with variable focal lenses, and adapted for adjusting a focal length of each lens based on the eye direction determined for the corresponding user's eye; and spectacles or mask provided with at least one active filter and adapted for adjusting a spectral transmission or a polarization filtering operation of this filter based on the eye direction determined for at least one of the user's eyes.

Again generally for the invention, the eyewear may comprise at least two sets each of at least three light sensors, each set having fields of view oriented so that this set is efficient for determining the eye direction for a position of the eyewear on the user's face, the respective eyewear positions that correspond separately to all light sensor sets being different from each other. For example, when the eyewear is of spectacle type, its positions may correspond to different locations of the spectacles along the user's nose.

Possibly, the eyewear according to the invention may comprise a corrective system configured to provide, to the processing unit, contextual data relating to a context of measured light intensity values by the at least three light sensors for a given determination of the eye direction, and the processing unit being configured to determine the eye direction further based on the contextual data.

The corrective system may comprise at least one additional sensor, with the contextual data being based on an output of the at least one additional sensor.

Alternatively or in addition, the corrective system may comprise a standalone device for sensing additional data relating to the eye direction of the user's eye, the corrective system being configured to determine an independent estimation of the eye direction based on an output of the standalone device and to provide the independent estimation to the processing unit.

Optionally, the at least three sensors may be configured for outputting the measured light intensity values at a given frequency and the at least one additional sensor may be configured for outputting the additional data at a frequency different from the given frequency.

Optionally, the corrective system may comprise an activation module for temporarily switching the corrective system from an inactive mode to an active mode upon detection of an event, said detection being based on an output of at least one sensor.

These and other features of the invention will be now described with reference to the appended figures, which relate to preferred but not-limiting embodiments of the invention.

BRIEF DESCRIPTION OF THE DRAWINGS

For clarity sake, element sizes which appear in these figures do not correspond to actual dimensions or dimension ratios. Also, same reference numbers which are indicated in different ones of these figures denote identical elements of elements with identical function.

DETAILED DESCRIPTION OF THE INVENTION

Figures 1, 2A, 2B:
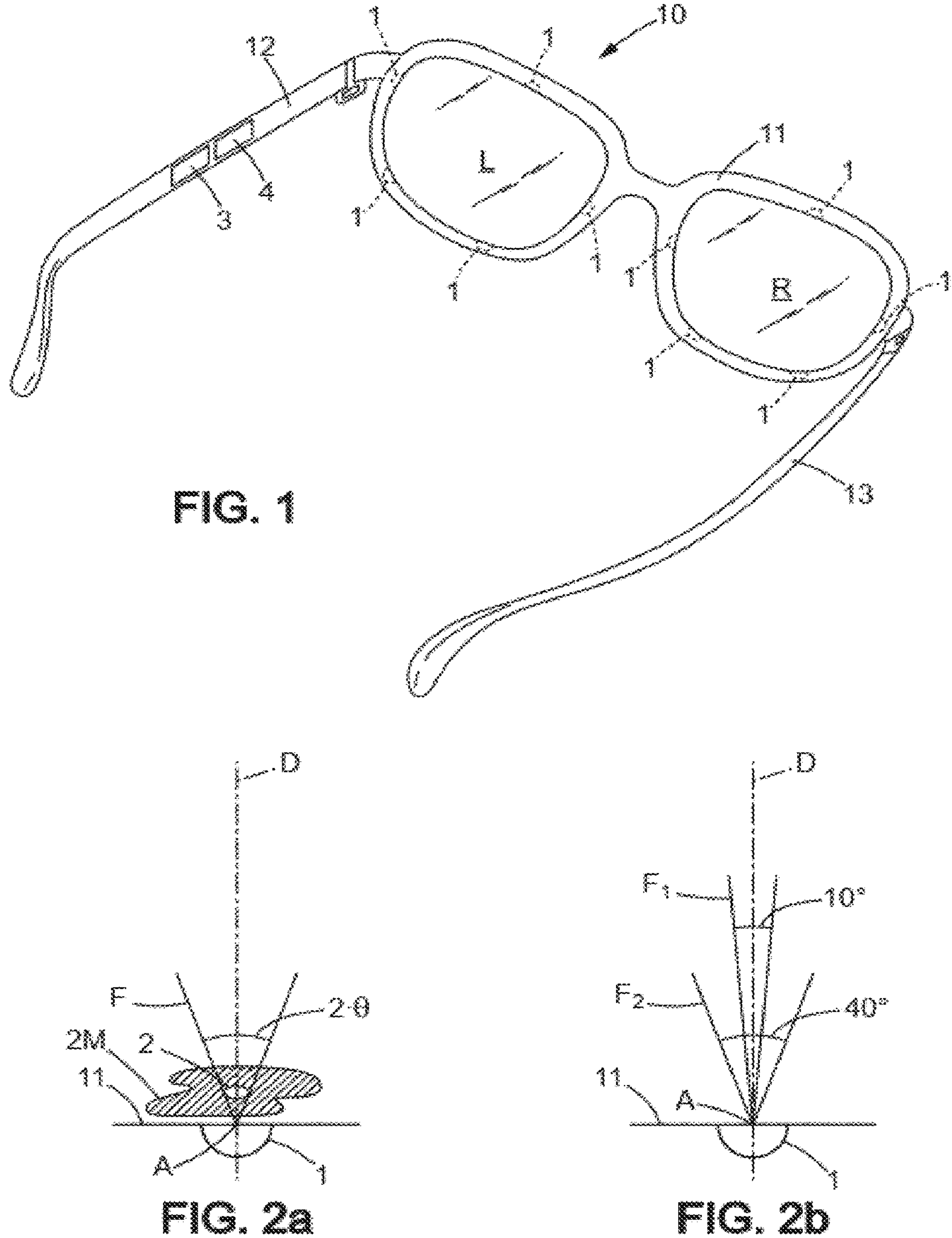
FIG. 1 is a perspective view of an eyewear according to the invention.
FIG. 2*a* is an enlargement of one light sensor used in the eyewear of FIG. 1.
FIG. 2*b* corresponds to FIG. 2*a* for a particular embodiment of the invention.

An eyewear in accordance with the present invention is generally denoted by reference number 10 in FIG. 1. In the embodiment illustrated, the eyewear 10 is comprised of a spectacle equipment with face-fitting frame 11, temples 12 and 13 and left and right see-through areas denoted L and R respectively. Each one of the see-through areas L and R is dedicated to one of the eyes of a wearer of the eyewear 10. In possible embodiments of the invention, eyeglasses may be accommodated in the frame 11 at the see-through areas L and R for producing any optical function including ametropia correction, active accommodation aid, active darkening, in particular for solar protection, spectral filtering, in particular active spectral filtering, polarization filtering, in particular active polarization filtering, and information display, in particular for augmented reality applications. Anyone will also understand that the function of determining the eye direction is not limited to using eyeglasses in the see-through areas L and R, and that applications exist that require determining the eye direction for purposes not implemented within the frame 11.

A plurality of light sensors 1, for example five light sensors, are arranged in the frame 11 at the peripheral limit of each of the see-through areas L and R. Alternatively, some of the light sensors 1 may be located at the nasal bridge of the frame 11 or in the temples 12 and 13, but locations close to the see-through areas L and R are preferred for the light sensors 1 oriented towards the wearer's eye. Each light sensor 1 may be comprised of a photodiode, but other light sensor types may be used alternatively. Each light sensor may also be combined with an optical filter, and/or an electrical amplifier. Each light sensor 1 is associated with a field of view F having an aperture value and an axial direction D (see FIG. 2*a*). According to the invention, the respective fields of view F of at least three of the light sensors 1 are oriented towards the left or right wearer's eye that corresponds to the see-through area L or R considered, with an aperture value that is comprised between 0.006 steradian and 0.22 steradian. Each field of view F has an apex A located at the corresponding light sensor 1, or more generally at the frame 11 considering some particular embodiments which will be described later. Each field-of-view cross-section increases when moving along the field-of-view axial direction D away from the apex A. The shape of each field of view F may be any in cross-section, including disk shape, square shape and elongated shape with longitudinal direction oriented in a selected manner. The shape of each field of view F may be determined by any means, including a small lens of any type, in particular refractive—or diffractive type, a hole with slanted peripheral wall or an aperture stop arranged above a photosensitive surface of the light sensor. FIG. 2*a* shows such light sensor 1 supported by the frame 11 with its field of view F determined by a hole 2 cut in a mask 2M which is arranged above the photosensitive surface of the light sensor. The mask 2M thus determines the axial direction D of the field of view F, its cross-sectional shape and its aperture value. In the example represented, the cross-sectional shape of the field of view F is circular, so that the field of view F has a conical shape with aperture angle $2\cdot\theta$. Preferably, this aperture angle $2\cdot\theta$ is comprised between 5° and 30°, preferably between 8° and 15°, for example equal to 10°. The field of view F is oriented towards the wearer's face, so as to contain at least part of the wearer's eye. In such embodiments of the invention, the apex A of each field of view F is located at the photosensitive surface of the corresponding light sensor 1. For enough sensitivity to the eye direction of the measured light intensity value which is outputted by each light sensor 1 that is oriented towards the user's eye, at least 30% of the field of view F of this light sensor, preferably at least 50%, is occupied by the wearer's eye.

In alternative embodiments, an optical fiber segment may be used between the photosensitive surface of each light sensor 1 and the corresponding field of view F. Then, the aperture value and the shape of the field of view F may be determined by the type of the optical fiber used, in particular its f-number value. Such embodiments allow placing the light sensors 1 in the frame 11 at distance from the see-through area concerned L or R and optically coupling the light sensors to the desired locations for the apex A of the fields of view F via the optical fiber segments.

It is also possible arranging a semi-reflecting holographic layer across part or all of the see-through area R or L for re-directing through reflection the fields of view F of the light sensors 1 towards the wearer's face. Such embodiments allow locating the light sensors 1 within recesses of the frame 11 around the see-through areas for aesthetic issues. The semi-reflecting holographic layer may be efficient in a narrow wavelength range for the light impinging on it, for example limitedly in a wavelength range of 4 nm (nanometer) to 10 nm width. This avoids that the holographic layer disturbs the wearer's color vision. Then, the light sensors 1 which are oriented towards the wearer's eye through reflection by the holographic layer may be preferably combined with a spectral optical filter that matches the holographic layer efficiency range.

Preferably, the whole information captured by the light sensors 1 has low redundancy. To this end, it is preferred that the axial directions D of all fields of view F do not converge to a single convergence point located in the wearer's eye, otherwise the symmetry of the iris would produce information redundancy. Hence, the fields of view F may be oriented so that their axial directions D exhibit at least two convergence points that are each common to at least two fields of view F, or so that at least some of the axial directions D do not cross any other one. For similar reason, overlaps between the fields of view F at the wearer's face are preferably low, in particular such that the sum of aperture values of field-of-view portions that are each common to at least two of the fields of view F is less than 40%, preferably less than 10%, of the sum of respective aperture values of all fields of view F.

In improved embodiments of the invention, the fields of view F may be associated in pairs having same axial direction D and substantially same field-of-view apex A, but with different aperture values within each pair, for example conical fields of view with angle values $2 \cdot \theta$ equal to 10° and 40° within each pair (see FIG. 2*b*). Such configuration of the fields of view provides more reliable detection information even when ambient light varies. Such improved embodiments may be obtained by distributing the light sensors 1 in pairs, with both light sensors of one and same pair that are close to one another. Alternatively, each pair of fields of view may be obtained by combining one light sensor with an active device suitable for varying the aperture value of the field of view. Such active device may be a variable focal length lens, of any type including variable membrane lenses or a liquid crystal lenses or variable refractive index lenses as examples. Then, the eyewear 10 comprises a controller for varying the aperture value quickly between two successive light intensity measurements, for example a first measurement with the angle value of 10° and a second measurement with the angle value of 40° performed immediately after the first measurement. FIG. 2*b* illustrates such operation, in which $F_1$ and $F_2$ denote both fields of view with same axial direction D and apex A but respective angle values of 10° and 40°.

The eyewear 10 may further comprise additional light sensors that are dedicated to assessing a light map of the wearer's surroundings or of the wearer's face. The fields of view of such additional light sensors are oriented away from the wearer's eye, for example away from the wearer's face or towards a portion of the wearer's face skin. The additional light sensors provide additional measured light intensity values which may be useful for separating contributions to the measured light intensity values that relate to the eye direction from other contributions due to the wearer's surroundings and to variations related to head movements of the wearer. Possibly, an inertial measurement unit (not represented) may also be accommodated in the frame 11 for sensing the head movements and allowing subtraction of contributions of the head movements in variations of the measured light intensity values which are outputted by those of the light sensors that are directed towards the wearer's eye.

Possibly, those of the additional light sensors that are oriented away from the wearer's face may be designed for assessing polarization features of some light existing in the wearer's surroundings. This may be useful for example if the wearer is close to or in the vicinity of a water surface. For example, two of these additional light sensors may have identical fields of view, but one without polarization filtering capability and the other one provided with a polarization filter. Such design for at least some of the additional light sensors may be useful for taking into account effects of significantly polarized light that is impinging onto the wearer's eye.

All light sensors 1 used in the eyewear 10 are preferably sensitive in the visible range, i.e. from 360 nm (nanometer) to 780 nm, and possibly sensitive to a limited part within the visible range. Therefore, suitable spectral filters may be combined with the light sensors 1, preferably filters that are identical for all these light sensors. It may be advantageous that those of the light sensors 1 that are oriented towards the wearer's face—skin portion or the eye—are arranged so that light received by these sensors does not pass through an eyeglass that is situated in the see-through area L or R when propagating between the wearer's face and the light sensor. These light sensors may thus be located outside the eyeglass in front of the posterior face of the eyeglass, close to its peripheral edge. However, for the additional light sensors which are oriented away from the wearer's face, they are preferably located so that light received by these additional sensors passes through the eyeglass for automatically taking into account modifications in the lightening of the wearer's face that are produced by the eyeglass. This is helpful in particular when the eyeglass is light-absorbing, including a photochromic eyeglass, polarization-filtering or has optical power. Such arrangements for all the light sensors further improve the reliability of the determination of the eye direction.

Preferably again, the light sensors 1 of the eyewear 10 may be combined with at least one filter suitable to discard contributions to the measured light intensity values that are associated with time-variations having frequencies equal to 50 Hz (hertz), 60 Hz, 100 Hz or 120 Hz. Such time-filtering avoids determining erroneously variations in the eye direction when the ambient light is artificial one. If artificial light with time-variations corresponding to one of the above-mentioned frequency values is detected, the light sensors may be controlled for performing their respective light intensity measurements simultaneously, so that the ambient light time-variations do not interfere with the actual eye direction in the measurements.

Each eye direction is determined from a set of measured light intensity values which are captured by the light sensors 1 simultaneously and are transmitted by these latter to a processing unit 4 (see FIG. 1). The processing unit 4 may be located within the frame 11, for example within one of the temples 12 and 13. A power source 3, for example an electrical battery, may also be accommodated in the frame 11 for supplying the processing unit 4 with necessary energy. The power source 3 may also be used for applying suitable bias voltage to the light sensors 1.

For increasing reliability of the determined eye direction, it is preferred to perform a pre-processing of the measured light intensity values outputted by those of the light sensors that are oriented towards the wearer's eye. Such pre-processing aims at correcting the measured light intensity values for effects of the surrounding light which may be reflected on the wearer's eye differently for one of the fields of view F compared to another one.

A first possible pre-processing only implements light sensors that are oriented towards the wearer's eye. For suppressing the effect of a general ambient light level, the measured light intensity values that are outputted by the light sensors may be transformed into normalized deviation values in the following manner. First, a mean value is computed for the measured light intensity values, then this mean value is subtracted to each of the measured light intensity values, and each subtraction result is further divided by the mean value. In this way, normalized deviation values are obtained which suppress the effect of the ambient light level on the further-processed values.

Second possibilities for pre-processing the measured light intensity values implement those of the light sensors 1—previously called additional light sensors—that are oriented towards the face skin of the wearer outside his eye, for example towards skin portions located on the left and right sides of the wearer's face. Then, the measured light intensity value that is outputted by one of the light sensors 1 oriented towards the wearer's eye may be reduced by an amount which depends mainly on the measured values outputted by the additional sensors having parallel axial directions D but oriented towards skin portions. All the measured values outputted by the additional light sensors 1 may also be taken into account for correcting the measured light intensity value that is outputted by one of the light sensors 1 oriented towards the wearer's eye, but major role is preferably assigned to those corresponding to axial directions D that have small angular differences with the eye-oriented light sensor considered.

A third possible pre-processing implement pairs of fields of view as illustrated in FIG. 2*b*. Each light sensor 1 performs a first measurement with field of view $F_1$, and immediately thereafter a second measurement with field of view $F_2$. Both measurements are preferably performed quickly after one another so that they correspond to same eye direction. Then, a difference is computed for each light sensor 1 between the first and second measurement, and the difference result constitutes the pre-processed values.

Fourth possible pre-processings implement additional light sensors that are oriented away from the wearer's face. For example, three to eight additional light sensors are dedicated to measure ambient light in different directions so as to assess a light map of the wearer's surroundings. Such light map allows inferring lighting spatial variations that affect the wearer's eye differently in each field of view, and then correcting for such spatial variations the measured light intensity values which are outputted by those of the light sensors that are oriented towards the wearer's eye, in a way similar to the second possibilities above. According to an improvement for assessing the light map more accurately, the invention eyewear may further accommodate an inertial measurement unit which allows separation of the ambient light spatial variations from the movements for the wearer's head.

Also possibly, several of the previous pre-processing modes may be combined for obtaining even more reliable eye direction determination. The eye direction is then determined from the pre-processed measured light intensity values.

Alternatively, it is possible not to implement any pre-processing onto some or all of the measured light intensity values and to determine the eye direction by inputting these measured light intensity values as produced by the corresponding light sensors into the algorithm for determining the eye direction.

Several algorithms may be used alternatively for determining the eye direction from the measured light intensity values, or from the pre-processed measured light intensity values. Such algorithms are known from the Man skilled in the art, so mentioning here some of them without describing them in detail is enough. Some of these algorithms are of regression type, in particular linear or polynomial regression, support vector regression, or of neural network type. Other algorithms such as nearest neighbor method, gaussian process, correlation method and 3D-modelling of the wearer's face and/or of the sensor arrangement may be used alternatively. Hybrid methods may also be used. In the present description, this step of determining the eye direction from the light intensity values, either as-measured or pre-processed, has been called processing step.

For operation of the eyewear in determining the eye direction, the processing unit may require carrying out a calibration step beforehand. Such calibration step may be useful for setting one or several parameters of the algorithm which infers the eye direction from the measured light intensity values. In particular, such calibration step may consist in acquiring labeled training sets of measured light intensity values and associating them with specified eye directions. Such calibration step may relate to general parameters that are independent from the wearer, such as the type of the eyewear, sensor calibration and locations, etc., but also parameters that relate to the wearer. Such latter wearer-depending parameters may concern eye color, skin color, face shape, ophthalmic correction, eyeglass type, wearer's position when reading a paper or climbing stairs, usual head movements, usual position of the eyewear on the wearer's face, etc. Possibly, a general training step may be implemented first, using a training dataset relating to several wearers, and thereafter an additional training step that relates individually to the wearer considered. The additional training step consists in adjusting parameters of the eye direction determination algorithm especially for the wearer, using a method which may be either the same as that for the general training step or a different one. For example, when this method is different from that of the general training step, the additional training step may consist in rescaling light intensity values and eye directions for the wearer. It is also possible in the additional training step to capture measured light intensity values only when the wearer is performing identified eye movements, and using these captured values to adjust some parameters of the algorithm implemented for eye direction determination. In such case, the additional training step may not use any training dataset.

When the eyewear is likely to fit on the user's face according to several positions, for example spectacles that may be located at two positions along the user's nose, it may be advantageous to provide it with two sets of light sensors, each appropriate for one of the wearing positions. In particular, the orientations of the fields of view may depend on the wearing position, for example through the separating distance between the light sensors and the user's eye. Thus, a first set of light sensors may be dedicated to the wearing position close to the user's face, and a second set of light sensors may be dedicated to the wearing position further from the user's face. Possibly, both light sensor sets may have at least one common light sensor whereas other ones are dedicated to only one of the sets. Selecting automatically one of the light sensor sets for determining the eye direction, based on at least some of the measured light intensity values, may also result from special aspects of the calibration step. Such selection of the light sensor set to be used may be replaced by a variable weighting that is applied by the processing unit onto all the measured light intensity values depending on the wearing position. Also possibly, the processing step can first estimate the eyewear position and secondly apply a mathematical model depending on the eyewear position. The mathematical model is then different for each eyewear position but uses all light sensors. The model used may induce less impact for some of the sensors compared to others.

Figures 3A, 3B:
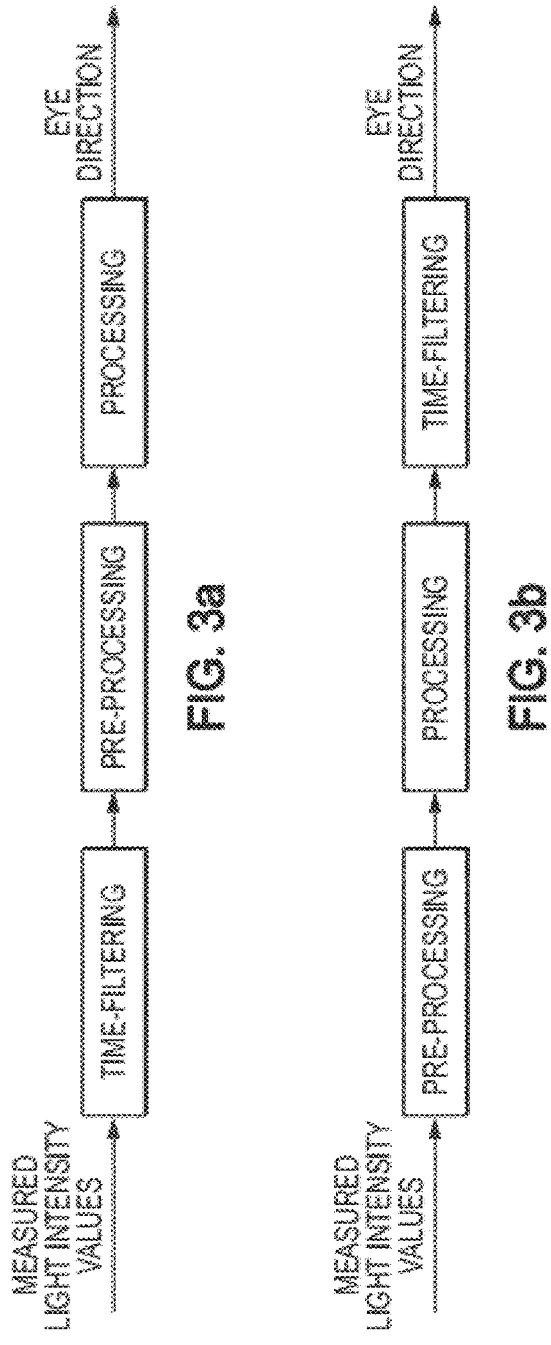
FIG. 3*a* is a diagram showing steps performed by a processing unit of the eyewear of FIG. 1.
FIGS. 3*b*, 4, 5 and 6 each correspond to FIG. 3*a* for alternative embodiments.

Further improvements in the reliability of the eye direction determined by the invention eyewear may be obtained by taking into account that the time-variations in the eye direction are continuous. To this end, a time-filtering, for example of Kalman-type, may be implemented either on the measured light intensity values which are outputted successively, or on eye directions which are determined successively. FIGS. 3*a* and 3*b* relate to such improvements, with the time-filtering performed on the measured light intensity values before the pre-processing step (FIG. 3*a*), or after the processing step (FIG. 3*b*). Alternatively, the time-filtering may be performed on the pre-processed measured light intensity values but before the processing step, or in combination with the processing step. Implementing a Kalman filter of predicting type may be useful when no eye direction can be determined actually, such actual determination being then replaced by the Kalman-predicted eye direction.

Knowledge of the instant eye direction is useful for many applications including protection against dazzling, polarization filtering, for instance polarization filtering limited to eye directions oriented downwardly, optical power modulation depending on focusing distance, augmented reality, informative eyewear or mixed reality and virtual reality eyewear, etc. For informative eyewear, the information is often not mobile but could be displayed only if or when the wearer is looking through a specific part of the lens. Depending on each application, the eyewear may have several forms including spectacles, goggles, a mask, for example a diving or skiing mask, a helmet, etc. Then, the eye direction may be used for controlling various functions such as electrochromic eyeglass darkening, polarization filter control, focus length modulation, display location, etc.

The light sensors may be affected by measurement disturbances such as a variation in light conditions or a slippage of the eyewear. Indeed, when the eyewear according to the invention slips, the point of view of the light sensors changes. Also, the amount of light perceived by the light sensors depends on the ambient light conditions, which may vary in time. Other possible measurement disturbances may include variation of the pupil size, movement of the eyelid, make-up, tired or wounded eye, eyelash flexibility, and the like. Measurement disturbances are generically called, in this document, measurement context, or more simply context. The context influences the way that the measurements by the light sensors of the main system vary according to the movements of the user's eye. Such variations may affect correlations between the measurements from the light sensors and the user's eye direction.

Additional robustness to light variation, to eyewear slippage, and more generally to measurement disturbances may be provided by a corrective system.

Figure 4:
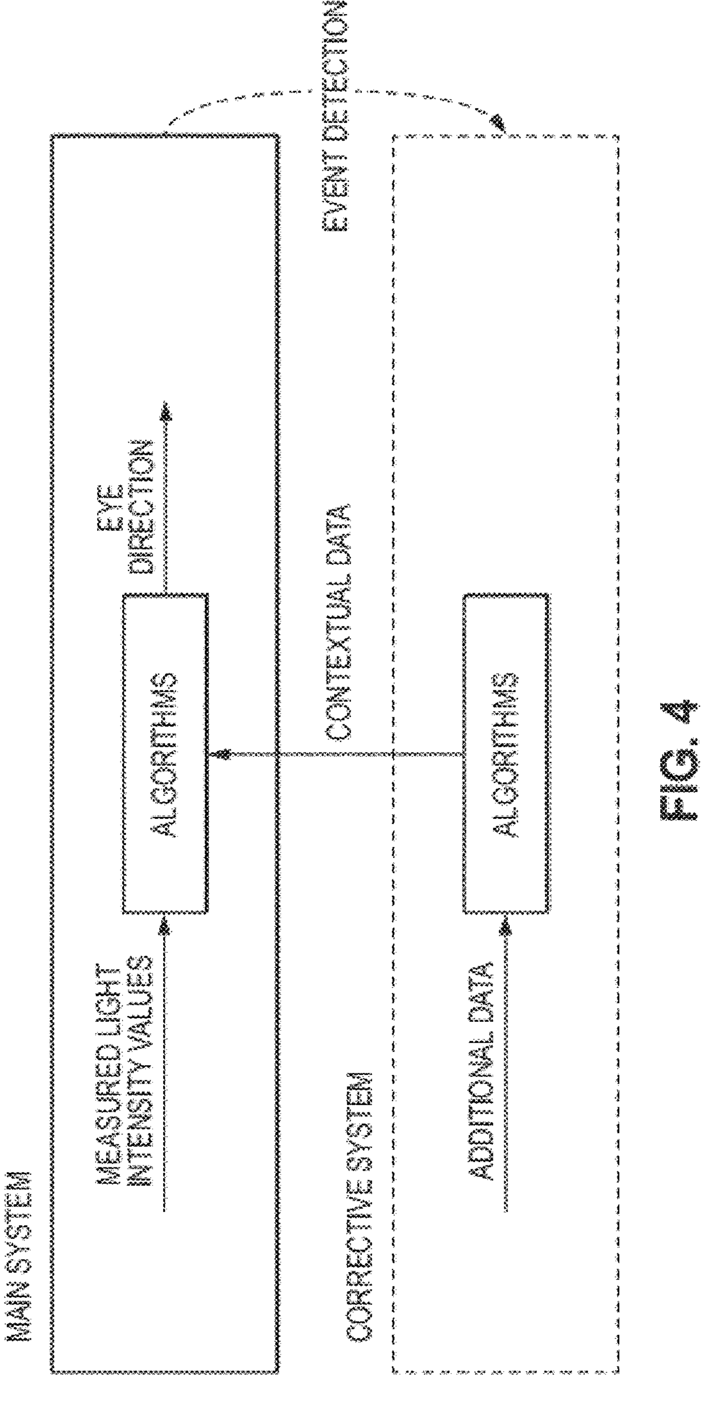
Figure 5:
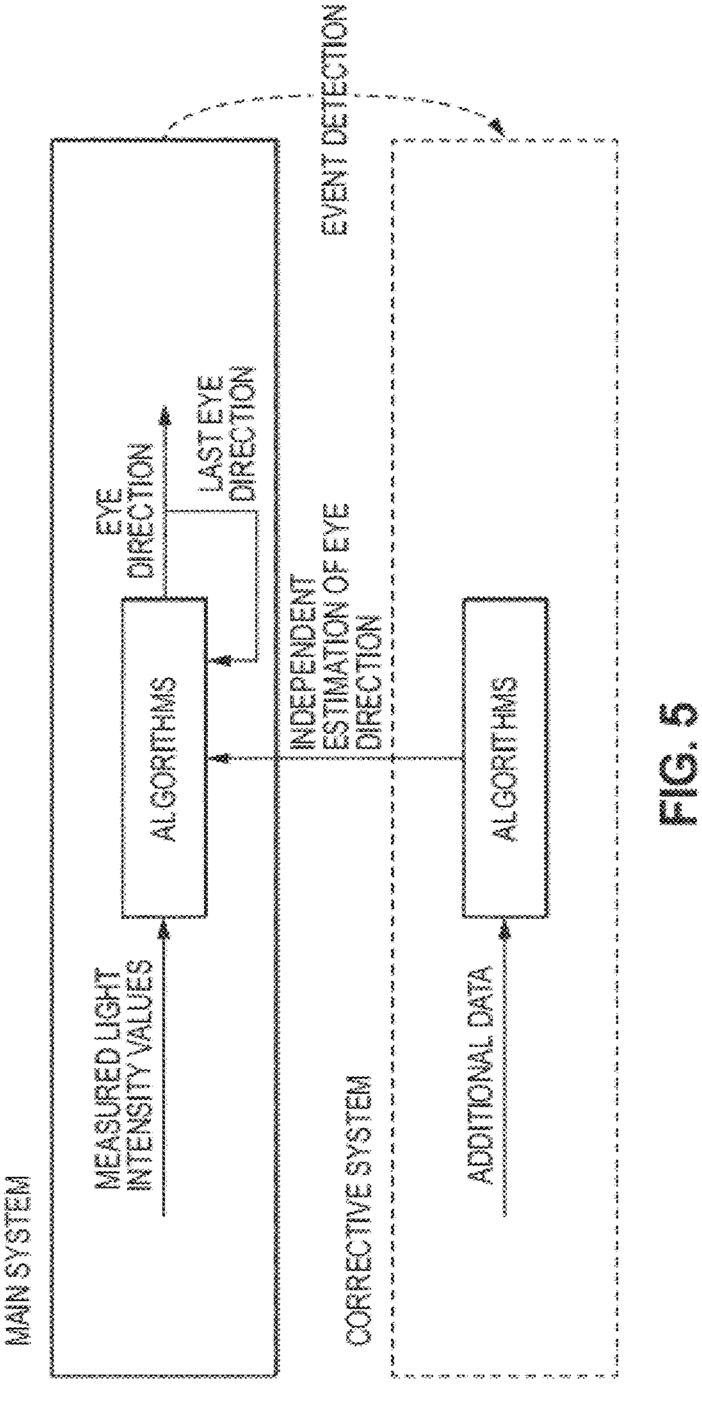
Figure 6:
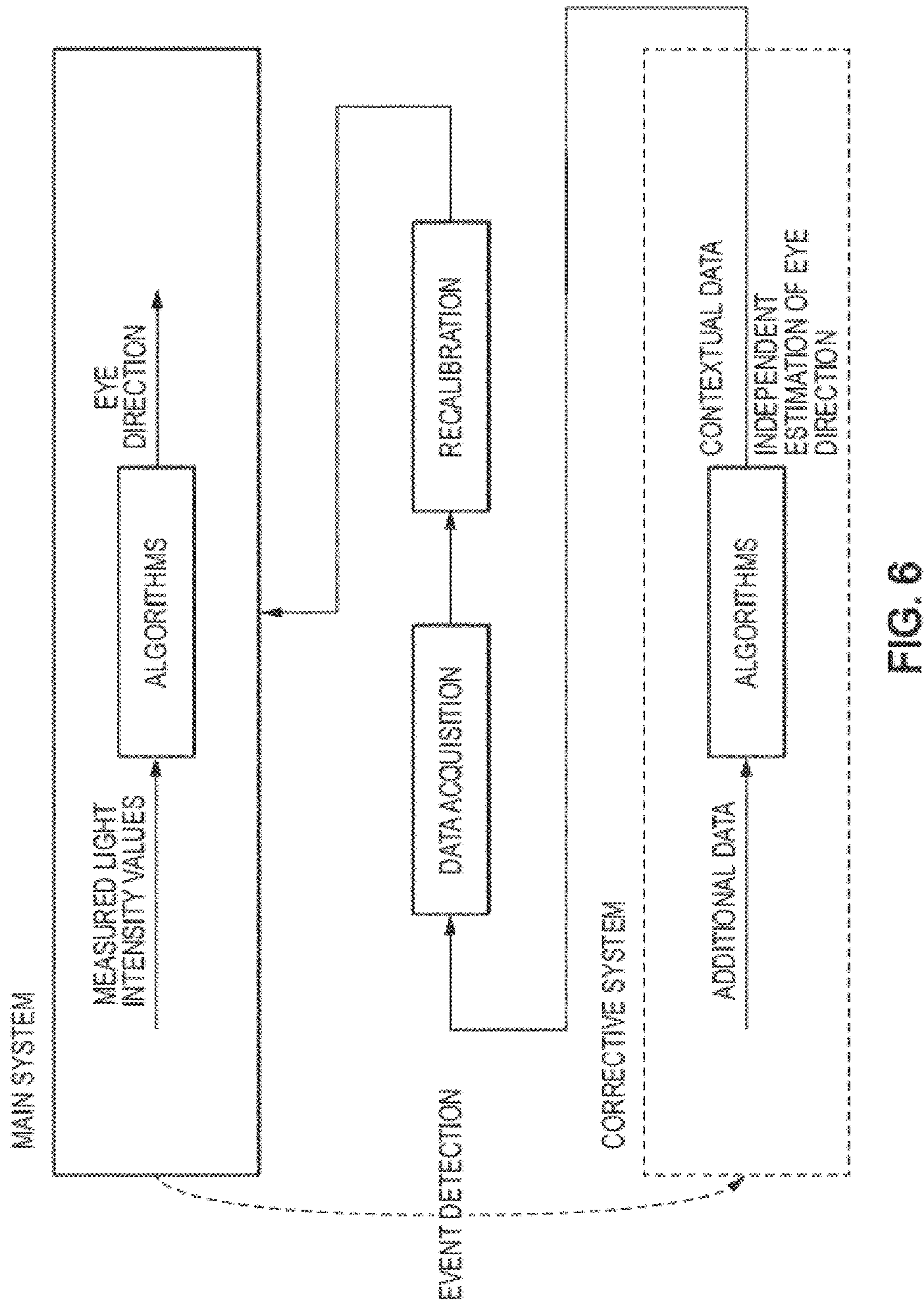

FIGS. 4 to 6 relate to such improvements, with an eyewear comprising a main system that comprises the at least three light sensors and the processing unit as described above, and that may be ran, for instance, at a desired frequency noted f1. The main system obtains as inputs measured light intensity values and determines as an output an eye direction of a user's eye, for instance according to FIG. 3*a* or FIG. 3*b*.

As depicted on FIG. 4, the eyewear may further comprise a corrective system configured to provide the main system with contextual data, which allows a more robust estimation by the main system of the direction of the user's eye. To do so, the corrective system comprises one or more additional sensors arranged in the eyewear. Such additional sensors are suitable for sensing additional data relating to context. The corrective system further comprises a processing module that receives the sensed additional data from the one or more additional sensors. The processing module determines contextual data based on the sensed additional data and provides the contextual data to the processing unit of the main system. The main system is further configured to receive the contextual data and to estimate the eye direction of the user's eye further according to the contextual data.

When a measurement disturbance is identified by the corrective system, the contextual data transmitted to the processing unit of the main system are indicative of the identified measurement disturbance. The processing unit may then decorrelate the measured light intensity values from the context. In other words, the processing unit may be configured to determine the eye direction of the user's eye by choosing a correct mathematical model depending on the context within a set of models, or by considering a model which uses context as input in addition to light measurements, or even by decorrelating disturbance from data before applying the model.

In a simple example, the corrective system may comprise an inertial measurement unit, being a known combination of sensors including accelerometers, gyroscopes and magnetometers. According to known methods, a movement of the eyewear or a head movement of the user wearing the eyewear may be detected and optionally characterized based on the combination of data sensed by the sensors of the inertial movement unit. Therefore, the processing module of the corrective system may provide to the processing unit of the main system, as contextual data, an indication that a movement of the eyewear or of the head of the user has been detected, or an identifier of a type, a direction, a magnitude, a speed, etc. of such movement.

In another example, the corrective system may comprise, as an additional sensor, a small, low power and lowresolution camera or array or matrix of photodetectors, that is arranged to be facing an eye of the user when the eyewear is normally worn by the user. By processing an image output by such additional sensor, the processing module of the corrective system may:

- deduce the position of the eyewear relatively to the user's face and detect eyewear slippage, and/or
- determine a lightmap indicating how the user face is lit up and detect a level of ambient light, and/or
- determine contextual data relating to other context elements, and/or
- estimate, independently from the main system, a direction of the eye of the user that is faced by such additional sensor.

In yet another example, the corrective system may be configured to detect eye blinks of an eye of the user. There are various known ways of detecting blinks based on inputs from sensors. Optionally, the corrective system may comprise one or more dedicated sensors for detecting such eye blinks. Alternatively, or in combination, eye blinks may be detected by processing the measured light intensity values output by the light sensors of the main system, possibly in real-time. During a blink, since the eye is closed, any measured light intensity values output by the light sensors only depend on context such as eyewear position or light environment and do not depend on eye orientation. The corrective system may then run an algorithm that can estimate information about the context using these measurements during eye blinks. As the user's eyes blinks regularly, the context may be updated regularly at each blink by the corrective system, and may be provided regularly to the main system in order to improve the robustness of the determination of the user's eye direction.

Some of the possible algorithms that may be implemented at the processing unit of the main system tend to generate a bias in the estimation of the eye direction of a user's eye. As depicted on FIG. 5, the corrective system may help reducing this bias by performing an independent estimation of the eye direction of the user's eye regularly and by providing the independent estimation to the processing unit of the main system.

For instance, the processing unit may be devoid of a tracking functionality. In such a case, a single estimation of the eye direction of a user's eye is performed by the processing unit of the main system per each new set of measurements received at a given time from the light sensors, without taking into account any temporal or dynamical effects. An independent estimation of the eye direction of the user's eye provided by the corrective system may be helpful to confirm consistent estimations by the main system and/or to dismiss any inconsistent or outlier estimations by the main system.

Alternatively, the processing unit of the main system may include a tracking functionality, based for instance on a Kalman filter, on a recurrent neural network or on any equivalent algorithm. Due to taking into account temporal or dynamical effects, a tracking functionality is prone to drifts, since an erroneous estimation of the eye direction of a user's eye at a given instant would also be used to estimate the eye direction of the user's eye at subsequent instants. An independent estimation of the eye direction of the user's eye provided by the corrective system may be helpful to recalibrate the main system and avoid such drifts.

To do so, the corrective system may comprise a standalone eye-tracker, in the sense of an eye-tracker that is separate from the main system. The standalone eye-tracker may be any known device capable of determining the eyeball direction based on inputs from sensors, and relying on a different technology than the combination of an arrangement of light sensors and of a processing unit according to the main system. The standalone eye-tracker comprises, at least, one or more additional sensors suitable to sense additional data related to the eye direction of the user's eye and a processing module configured to receive the additional data from the additional sensors, determine the independent estimation of the eye direction based on the sensed additional data, and provide the independent estimation to the processing unit of the main system.

In an example, the standalone eye-tracker may comprise one or more infrared light sources, such as LED, arranged to illuminate an eye of the wearer, a set of infrared photodetectors arranged to sense the infrared light reflected by the eye of the wearer, and a processing module configured to collect the outputs of the set of infrared photodetectors. Based on a mathematical model linking infrared light measurements and eye direction, the processing module can determine eye direction from infrared lights measurements and then deduce the resulting disturbance within the visible light measurement. By knowing this disturbance, it is possible to decorrelate visible light measurements from light disturbance or to introduce this disturbance within the mathematical model to adapt the model to this new lighting condition. Optionally, the measuring step of said one or more infrared light sources may be modulated to allow performing synchronous detection with the light sensors of the main system, in order to remove disturbance due to light variation at lower frequencies than the chosen modulation.

In yet another example, the standalone eye-tracker may comprise one or several interferometer sensors based on laser feedback interferometry. From such measurement sensors, it is possible to deduce the observed target velocity, the distance between the sensor and the target, the light phase and the light polarization. Those data may be processed by a processing module to determine the eye velocity, the eye position relatively to glasses and the user line of sight. Optionally, these sensors may be combined with a 2D rotating micro-mirror (MEMS) to scan the eye region to obtain a signal which can be presented as a 2D image of the eye.

In yet another example, the standalone eye-tracker may comprise an infrared laser with a 2D rotating micro-mirror (MEMS) to scan the eye region, and with one or more photodetectors measure the laser reflection on the user's eye. As shown by recent studies, this system enables to generate an image of the eye region, which may be processed to deduce for instance eyewear slippage and/or eye direction of the user's eye.

Both functionalities of providing contextual data as depicted on FIG. 4 and providing an independent estimation of the eye direction of a user's eye as depicted on FIG. 5 are not mutually exclusive. In other words, the corrective system may comprise all the required additional sensors to provide not only an independent estimation of the eye direction of a user's eye, but also contextual data.

Some of the possible examples of corrective systems described above may be more consuming than the main system due to an embedded light or a power consuming component (camera, MEMS). In addition, there is a remaining uncertainty on health security regarding the use of incoherent infrared light source or laser directed to the eye and the retina for whole days (more than 8 hours) and for several years.

Regarding these two reasons, it is suggested to use the corrective system only at a low frequency or during a short time frame following a given event detection. In an embodiment, the corrective system is ran at a frequency that is different from the desired frequency f1 that the main system is ran at. For instance, the corrective system may be configured to obtain, from the one or more additional sensors, the additional data at a frequency f2 lower than f1. The lower frequency f2 allows minimizing energy consumption by the corrective system. With this configuration, the corrective system may automatically and periodically monitor any possible occurrences of measurement disturbances during normal operation of the main system, and may automatically and periodically monitor the eye direction of a user's eye in parallel of the main system.

Instead or in addition, the corrective system may have an inactive, or standby, mode and at least one active mode that is activated only temporarily, for instance in response to a detection of an event. The corrective system only provides the additional data to the main system when in the active mode. The inactive or standby mode contributes to minimizing energy consumption by the corrective system. Event detection may be performed at the processing unit and may be based, for example, on a sudden variation in measurements obtained over time from a given available sensor (such as a light sensor of the main system), and/or on a detection of a head movement by an inertial measurement unit arranged in the eyewear, and/or on a low level of trust, as assessed by an artificial intelligence based on the available data output by the available sensors, in the eye direction estimation provided by the processing unit. Event detection may be performed by comparing the data received as inputs by the processing unit and/or the data provided as outputs by the processing unit to various data patterns that may be associated to corresponding types of events in an event database.

The corrective system may also be advantageous for an initialization or a recalibration of the main system, as depicted on FIG. 6.

A recalibration procedure of the main system may be conducted periodically or be triggered by an event. An example of criterion defining such an event is when the pertinence, or estimated level of trust associated by an artificial intelligence to the estimation of the eye direction provided by the main system remains below a given threshold even after contextual data have already been recently received from the corrective system and processed by the main system. However, the recalibration procedure should not be applied too frequently to avoid a high-energy consumption.

Such a recalibration procedure involves temporarily activating the corrective system. An initial activation of the main system may also be interpreted as an example of event leading to a temporary activation of one or more functionalities of the correction system as part of an initialization procedure.

To perform an initialization or recalibration procedure of the main system, it is necessary to acquire a substantial amount of additional data, which may comprise raw sensor measurements, contextual data such as an eyewear position or orientation or a lightmap of a user's eye and/or an independent estimation of the eye direction of the user's eye. This additional data may be furnished by the corrective system and its embedded sensors. In order to minimize the time length of the initialization or recalibration procedure, it is desirable to quickly acquire a sufficient quantity of data.

The corrective system may then be ran at a frequency f3 higher than f1 during a narrow time interval corresponding to the acquisition of the additional data required for the initialization or recalibration algorithm to select, determine or update a mathematical model used by the processing unit of the main system. Said update may include for instance optimizing the mathematical model for a current context based on the contextual data. Said update may further rely on the independent estimation of the eye direction, for example by using said independent estimation as a criterion for selecting or determining the mathematical model, and/or as an offset in a predetermined or preselected mathematical function of the mathematical model, and/or as a coefficient or as a weighted value in a predetermined or preselected mathematical model.

The frequency higher than f1 may correspond to a dedicated active mode, namely an accelerated acquisition mode. After the additional data required for the continuation of the initialization or recalibration procedures is obtained, the frequency of the data acquisition by the additional sensors of the corrective system may be reduced by automatically switching the corrective system to another mode, which may be another active mode or the inactive or standby mode.

During the initialization or recalibration procedure, the main system may continue running in parallel, based on a default or pre-update mathematical model.

The invention claimed is:

1. An eyewear configured to fit a user's face and for determining an eye direction of a user's eye, said eyewear comprising:
- at least three light sensors arranged in the eyewear for said user's eye, each of said light sensors being configured to output, for each determination of the eye direction, at least one measured light intensity value that corresponds to ambient light originating from surroundings of the user outside the eyewear and reflected or scattered by the user's face within a field of view effective for said light sensor; and
- processing circuitry configured to receive the measured light intensity values for each determination of the eye direction, and determine the eye direction from said measured light intensity values,
- wherein the light sensors are arranged so that, when the eyewear is worn by the user:
  - each field of view relating to one of the light sensors has an apex at the eyewear and a cross-section increase direction oriented towards the user's face, the field-of-view cross-section increasing continuously from the eyewear towards the user's face,
  - each field of view contains at least part of the user's eye, and
  - each field of view has an integrated aperture value between 0.006 steradian and 0.22 steradian, and the user's eye occupies at least 30% of said field of view,
- the eyewear further comprises additional light sensors with respective fields of view oriented away from the user's eye when the eyewear is worn by the user, and configured to assess a light map of the user's surroundings or of the user's face, and
- the processing circuitry is further configured to determine the eye direction from the measured light intensity values relating to the light reflected or scattered by the user's eye in combination with the light map as assessed by the additional light sensors.

2. An eyewear configured to fit a user's face and for determining an eye direction of a user's eye, said eyewear comprising:
- at least three light sensors arranged in the eyewear for said user's eye, each of said light sensors being configured to output, for each determination of the eye direction, at least one measured light intensity value that corresponds to ambient light originating from surroundings of the user outside the eyewear and reflected or scattered by the user's face within a field of view effective for said light sensor; and processing circuitry configured to receive the measured light intensity values for each determination of the eye direction, and to determine the eye direction from said measured light intensity values, wherein the light sensors are arranged so that, when the eyewear is worn by the user:

each field of view relating to one of the light sensors has an apex at the eyewear and a cross-section increase direction oriented towards the user's face, the field-of-view cross-section increasing continuously from the eyewear towards the user's face, each field of view contains at least part of the user's eye, and each field of view has an integrated aperture value comprised between 0.006 steradian and 0.22 steradian, and the user's eye occupies at least 30% of said field of view, and the eyewear further comprises a corrective system configured to provide, to the processing circuitry, contextual data relating to a context of measured light intensity values by the at least three light sensors for a given determination of the eye direction, and the processing circuitry is further configured to determine the eye direction further based on the contextual data.

3. The eyewear of claim 2, wherein the corrective system further comprises at least one additional sensor and the contextual data are based on an output of the at least one additional sensor.

4. The eyewear of claim 2, wherein the corrective system further comprises a standalone device for sensing additional data relating to the eye direction of the user's eye, the corrective system being configured to determine an independent estimation of the eye direction based on an output of the standalone device and to provide the independent estimation to the processing circuitry.

5. The eyewear of claim 2, wherein the at least three sensors are configured for outputting the measured light intensity values at a given frequency and the at least one additional sensor is configured for outputting the additional data at a frequency different from the given frequency.

6. The eyewear of claim 2, wherein the corrective system further comprises an activation module for temporarily switching the corrective system from an inactive mode to an active mode upon detection of an event, said detection being based on an output of at least one sensor.

* * * * *